(12) United States Patent
Blum et al.

(10) Patent No.: US 6,405,165 B1
(45) Date of Patent: Jun. 11, 2002

(54) MEDICAL WORKSTATION FOR TREATING A PATIENT WITH A VOICE RECORDING ARRANGEMENT FOR PREPARING A PHYSICIAN'S REPORT DURING TREATMENT

(75) Inventors: Thomas Blum, Neunkirchen; Dirk Birrenbach, Heroldsbach; Thomas Reichert, Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/261,930

(22) Filed: Mar. 3, 1999

(30) Foreign Application Priority Data

Mar. 5, 1998 (DE) .......................................... 198 09 563

(51) Int. Cl.[7] .............................................. G10L 21/00
(52) U.S. Cl. ...................................... 704/235; 704/275
(58) Field of Search ................................ 704/270, 200, 704/207, 235, 275, 270.1

(56) References Cited

U.S. PATENT DOCUMENTS

| | | | | |
|---|---|---|---|---|
| 4,989,253 A | * | 1/1991 | Liang et al. ................. | 381/110 |
| 5,303,148 A | * | 4/1994 | Mattson et al. ............. | 600/437 |
| 5,544,745 A | * | 8/1996 | Famorca ..................... | 206/320 |
| 5,772,585 A | * | 6/1998 | Lavin et al. ................. | 600/300 |
| 5,970,457 A | * | 10/1999 | Brant et al. .................. | 704/275 |
| 6,122,614 A | * | 9/2000 | Kahn et al. .................. | 704/235 |
| 6,173,259 B1 | * | 1/2001 | Bijl et al. ............... | 704/235 Q |

FOREIGN PATENT DOCUMENTS

| | | | | |
|---|---|---|---|---|
| DE | 3032693 | 5/1990 | ........... | A61C/19/00 |
| DE | 43 31 710 | 3/1995 | ........... | H04M/3/50 |
| DE | 197 14 984 | 11/1997 | .......... | A61G/13/00 |
| EP | 180047 A2 | * 5/1986 | ............. | G06F/3/16 |

* cited by examiner

*Primary Examiner*—Richemond Dorvil
(74) *Attorney, Agent, or Firm*—Schiff Hardin & Waite

(57) ABSTRACT

A medical workstation for treatment of a patient has a device for the electrical registration of voice signals, a device for continuously storing the registered voice signals and a communication path for the transmission of the registered voice signals from the device for registration to the device for storing the voice signals.

5 Claims, 2 Drawing Sheets

MEDICAL WORKSTATION FOR TREATING A PATIENT WITH A VOICE RECORDING ARRANGEMENT FOR PREPARING A PHYSICIAN'S REPORT DURING TREATMENT

BACKGROUND OF THE INVENTION

1. Field of the Invention

The present invention is directed to a medical workstation for treating a patient.

2. Description of the Prior Art

German OS 197 14 984, for example, discloses a medical workstation in the form of a surgical-operative workstation. The workstation has an integrated device and operating unit that with a common housing in or at which a number of devices or device components, a central control unit, a central operating unit, etc., are accommodated or arranged. The operating unit can also contain a unit for voice control. The integrated device and operating unit, provides working and moving space for personnel working at the workstation and, for example, treating a patient.

After a treatment of a patient in the form of an examination, therapy administration or an operation, the attending physician usually produces a physician's report which documents the examination results, the therapy progress, or the course of the operation. This physician's report is added to the patient's file and is thus available for further physicians given renewed treatments of the patient.

Producing such a physician's report current ensues only after the examination, therapy administration or the surgical intervention. A disadvantage is that a time span of several hours or even days can intervene between the treatment of the patient and the preparation of the physician's report due to a heavy workload of the physician. This results in a risk that the information relating to the treatment, particularly in stress situations, could slip from the physician's memory, and thus would not be added to the file, possibly to the detriment of the patient. A further disadvantage of this procedure is that the physician must again expend time after a treatment of a patient in order to recapitulate the medical event and prepare the physician's report.

German OS 43 31 710 discloses a general purpose apparatus with means for dictation, means for transmission of the spoken voice signals and with a reception means that preferably comprises a voice recognition means. The apparatus serves the purpose of producing and commenting on text documents as well as for sending and receiving text documents via a telecommunication means.

SUMMARY OF THE INVENTION

An object of the present invention is to provide a medical workstation of the type initially described wherein the physician can already prepare at least a draft of the physician's report during the treatment of a patient.

This object is inventively achieved in a medical workstation for treating a patient allowing for registering information during the treatment of the patient by a device for electrical registration of voice signals, device for continuously storing the registered voice signals, and a communication path for the transmission of the registered voice signals from the device for registration to the storage device. With the invention, a physician can already document the course of the treatment or prepare a physician's report during the treatment of a patient, quasi online, by speaking appropriate information into the device for electrical registration of voice signals, for example into a microphone. The device for registering voice signals is connected via the transmission path to the device for the continuously storing of the registered voice signals. The storage of the voice signals can ensue electronically in the form of an analog or digital storage of the voice signals or in the form of storage of the voice signals on paper by printing out the voice signals after they are registered. A physician's report spoken during a treatment of a patient and registered is thus either present on paper or, preferably, electronically stored and can be unproblemmatically further-processed, i.e. acoustically and/or visually reproduced, amended, corrected or printed out and added to a patient file. An advantage of the inventive apparatus is thus that the time that the physician must expend for preparing physician's reports is clearly reduced by the possibility of online documentation during a treatment since the apparatus function quasi parallel in time with the treatment, i.e., the physical, simultaneously performs a diagnosis and registers the results or conclusions. Moreover, differing from the conventional practice, namely being compelled to produce physician's reports only after a treatment, the immediate preparation of physician's reports during a treatment prevents information relating to the treatment from being unintentionally lost, particularly in stressful situations of the appertaining physician, and thus possibly not being reflected in a physician's report to the detriment of the patient.

In one version of the invention the device for electrical registration of the voice signals is arranged so as to be carried by a person substantially in the region of the mouth of the person. Such an attachment of the device for registration of the voice signals has the advantage that the sound level of the registered ambient noises is significantly lower than, for example, the words of a physician spoken and registered during the treatment, so that a clear distinction is possible between the ambient noises and the spoken words of the physician.

In another embodiment of the invention the transmission path for the voice signals is formed by an electrical connecting line. The employment of a connecting line for the transmission of the voice signals between the device for registration and the storage device offers the advantages of being economical and not being especially susceptible to noise signals that could cause transmission errors.

In a further embodiment of the invention the transmission path for the voice signals employs wireless transmission from a transmission unit allocated to the device for registering the voice signals and a reception unit allocated to the storage device. The employment of wireless transmission and reception units for signal transmission offers the advantage that is very comfortable for the user since no connecting cable, that could possibly disturb the attending physician, is present. The wireless transmission of the voice signals can ensue, for example, with infrared light or electromagnetic radio waves.

In another version of the invention, the device for continuously storing the voice signals is a pickup unit provided with a storage medium, so that the voice signals stored on the storage medium can be acoustically reproduced. For example, the pickup unit can be a cassette tape recorder and the storage medium can be a tape cassette. After a treatment of a patient during which, for example, a physician has recorded the cassette, this cassette can be given to a typist for transcribing the physician's report stored on the cassette, so that the physician need not expend any further time for the recapitulation of the course of the treatment and the subsequent production of the physician's report. The physician's report written by the typist merely has to be reviewed by the physician, with little time expenditure, corrected as needed, and, finally, signed. The pickup unit can also be a computer that, for example, contains a circuit board of the type known comprises what is referred to as a sound card for the registration and playback of acoustic signals and a memory, for example a hard disk or magnetic drives provided with storage media etc. In this case, the voice signals can be digitally stored on one of the storage media and, for example, can be acoustically reproduced with the sound card and speakers of the computer.

In a preferred embodiment of the invention the device for continuously storing of the voice signals has a speech recognition system allocated thereto. Such a speech recognition system can, for example, be a computer equipped with appropriate hardware, for example, a sound card, and operated with a suitable software. The speech recognition system functions such that, for example, the voice signals spoken by a physician during the treatment are converted into a text file after the transmission to the speech recognition system, for example a data file in the known Word format of Microsoft, i.e. a written physician's report, and are stored. This can be subsequently presented to the physician, corrected as needed by the physician and ultimately signed by the physician, so that it can be added to the patient's file. The storage of the voice signals in a data file also offers the advantage that the data file can be added to a data bank containing patient data, for example in a hospital information archiving system, and the data of the data file can be combined with data of the patient, for example registered image data, physiological or personal data of the patient, that are stored in other data files in the data bank, i.e. new data files can be produced using the various patient data for physician's reports.

DESCRIPTION OF THE PREFERRED EMBODIMENTS

Figure 1:
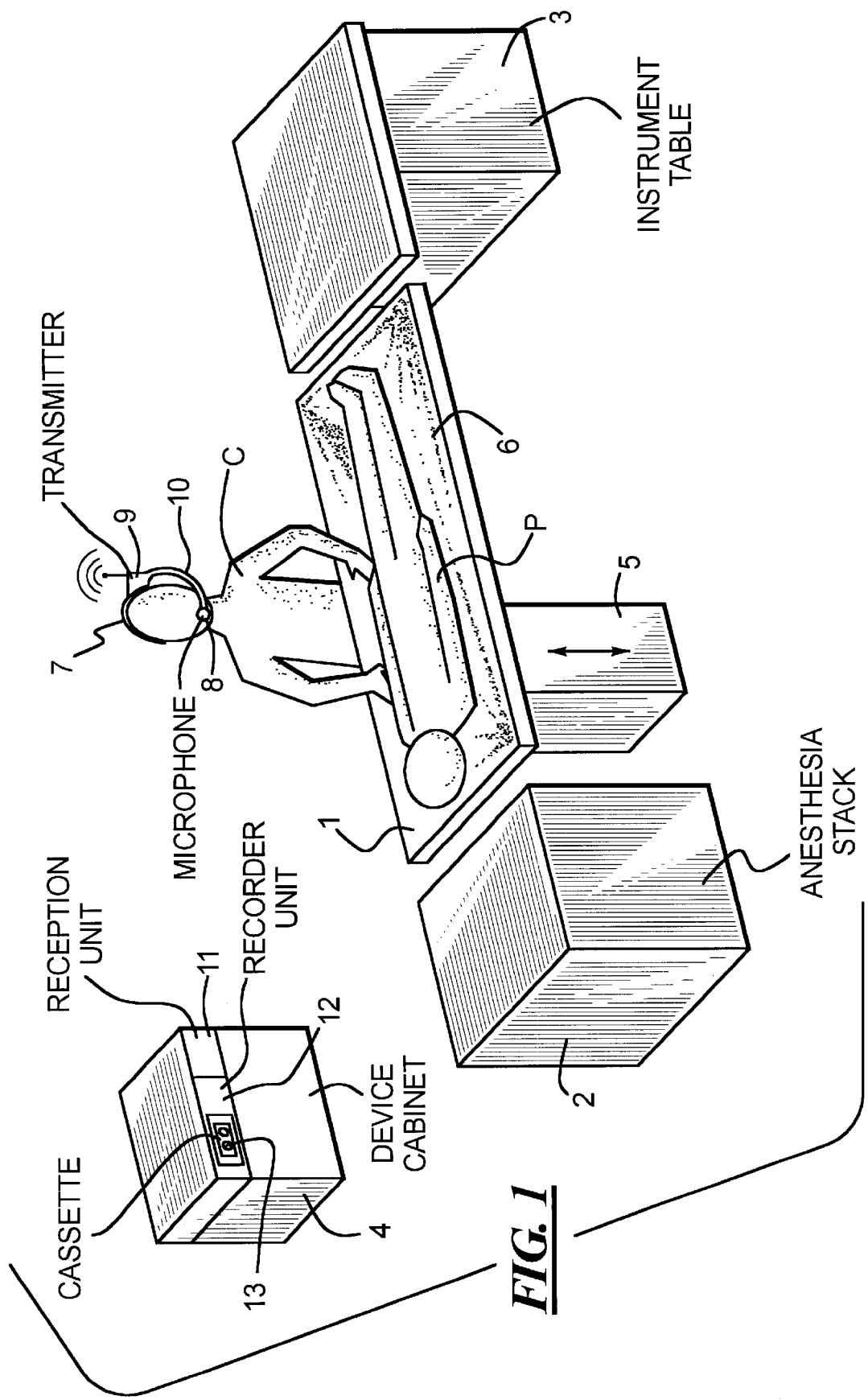
FIG. 1 shows a first embodiment of an inventive medical workstation with a device for online documentation during a treatment.

In the exemplary embodiment of a surgical workstation shown in FIG. 1, the workstation includes a patient support table 1, an anesthesia stack 2, an instrument table 3 and a device cabinet 4.

The patient support table 1 has a vertically adjustable lifting column 5 and a patient support plate 6 on which a patient P is supported. The anesthesia stack 2, which includes devices for anesthetization, de-anesthetization and for monitoring the life functions of the patient P in a known way that is not shown, and the instrument table 3 that keeps instruments, applicators and operating material for the surgical procedure ready, also in a known way that is not shown, are arranged at the patient support table 1 in a known way.

In a way that is known but likewise not shown, the device cabinet 4 contains devices or device controls for medical-technical devices, for example an ultrasound device, a rinsing/suction pump controller, an insufflator, a high-frequency unit, a cold light source, etc. The devices have respective applicators, for example an ultrasound head, a rinse/suction applicator, an insufflation applicator, a high-frequency scalpel, a cold light, that are connected to the corresponding medical-technical devices or device controllers via corresponding connecting lines. The applicators are kept on hand on the instrument table 3 for a surgeon C working at the workstation.

In the present exemplary embodiment, the surgeon C carries a device 7, such as a unit worn in the head, at which a microphone 8 for the registration of voice signals of the surgeon C is arranged. The microphone 8 is arranged at the device 7 so as to be located in the region of the mouth of the surgeon C. This results in the sound level of the voice signals of the surgeon on C picked up by the microphone 8 being significantly higher than the sound level of the ambient noises picked up by the microphone 8, so that a clear distinction is possible between the voice signals of the surgeon C and ambient noises.

A transmission unit 9 that is connected to the microphone 8 via a line 10 is also arranged at the device 7. Via the line 10, the voice signals of the surgeon C picked up by the microphone 8 and converted into electrical signals are transmitted to the transmission unit 9 that transmits (broadcasts) these signals wirelessly to a reception unit 11 arranged in the device cabinet 4, for example in the form of electromagnetic waves.

The reception unit 11 is connected to a recorder unit 12, likewise arranged in the device cabinet 4, to which the reception unit 11 communicates the voice signals received from the transmission unit 10. The recording unit 12 contains a cassette 13 as a storage medium on which the voice signals communicated from the reception unit 11 are continuously stored and from which these signals can be acoustically played back.

By means of the microphone 8, the transmission unit 9, the reception unit 11 and the recording unit 12, thus, the surgeon C can prepare a physician's report online during a treatment of the patient P, this being stored on a tape in the cassette 13. After the treatment of the patient P, the cassette 13 can be given, for example, to a transcriber who types the physician's report by listening to the cassette 13. The surgeon C can subsequently amend this draft, correct it as needed and ultimately sign it, and need not expend any noteworthy amount of time after the treatment of the patient P for the recapitulation of the treatment and the preparation of the physician's report.

Figure 2:
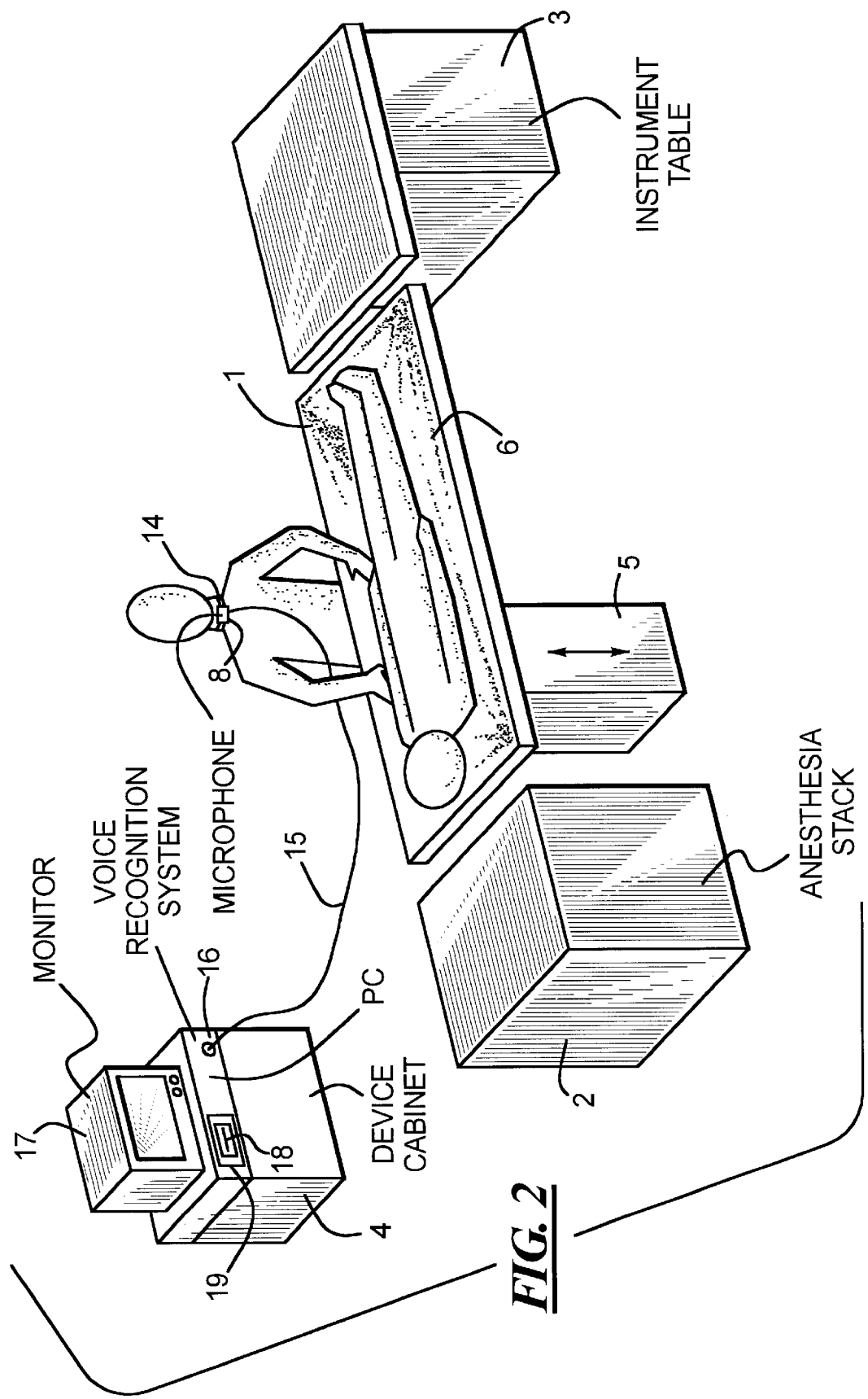
FIG. 2 shows a second embodiment of an inventive medical workstation with a device for online documentation during a treatment.

FIG. 2 shows a second embodiment of the inventive workstation, wherein components of the workstation of FIG. 2 that are substantially structurally and functionally the same as components of the workstation of FIG. 1 are provided with the same reference characters.

Differing from the workstation of FIG. 1, the microphone 8, which can also be a laryngophone, is carried at a device 14 that is arranged around the neck of the surgeon C. The microphone 8 is again arranged in the region of the mouth of the surgeon C so that the voice signals of the surgeon C registered by the microphone 8 during the treatment of the patient P can be clearly distinguished from registered ambient noises.

In the exemplary embodiment of FIG. 2, the microphone 8 is connected to a voice recognition system 16 via a connecting line 15. In the this exemplary embodiment, the voice recognition system 16 is a computer in the form of a personal computer PC and a monitor 17, the PC being operated by appropriate hardware, for example as sound card, for the pickup and reproduction of acoustic signals, and by suitable software for voice recognition and subsequent digital storage of the voice signals. The voice signals of the surgeon C registered during the treatment of the patient P by the microphone 8 and converted into electrical signals are thus transmitted to the PC via the connecting line 15 and are converted thereat into written words. These can either be directly displayed on the monitor 17 of the PC or can be stored in a text file, for example a data file in the known Word format of Microsoft. The data file can in turn be stored on a digital storage medium of the PC, for example on a hard disk of the PC, on a tape drive or on a diskette 18 that is inserted into a diskette drive 19 of the PC, and can also be printed out. In this way, a subsequent reworking of the physician's report produced during the treatment of the patient P is possible.

It is especially advantageous that the data file can be added to a patient data bank, for example the hospital information system, in which data files of registered image data, for example X-ray or ultrasound exposures of the patient, physiological and personal data of the patient, can be stored. In this way, the patient data stored in the various data files can be combined with one another, i.e. new data files can be prepared using various patient data, for example for producing a physician's report. The PC is for this purpose preferably connected to a data network for the exchange of patient data with the data bank.

The registered voice signals, moreover, can also be stored on suitable storage media of the PC so that, for example, they can be acoustically played back with the sound card and speakers of the PC.

The microphone 8, moreover, need not necessarily be arranged in the area of the mouth of the surgeon C but can alternatively be arranged at some other location (room microphone) of the medical workstation, but this has the disadvantage that room noises may possibly be recorded just as strongly as the voice signals of the surgeon C, resulting in more extensive post-processing of the physician's report being required.

The above-described storage media for storing the physician's report are only an example. Thus, other analog or digital storage media, for example magneto-optical storage media, can be employed for storing the physician's report.

Mixed forms of the workstations 1 and 2 are also possible. In the case, for example, of the workstation shown in FIG. 1, the transmission of the voice signals can ensue to a speech recognition system or, given the workstation shown in FIG. 2, the wireless transmission of the voice signals can ensue with transmission and reception devices.

The invention was described above with reference to the example of a surgical station, however, it is not limited to surgical workstations but can also be employed in diagnostic or therapeutic workstations.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical workstation for treating a patient, comprising:
    means for registering information during treatment of a patient for preparing a physician's report about the treatment including means for electrically registering voice signals;
    means for continuously storing registered voice signals from said means for electrically registering voice signals, said means for continuously storing registered voice signals including a speech recognition system for converting said voice signals into an editable text file, said means for continuously storing registered voice signals further including a data bank of a hospital information archiving system for storing said text file; and
    means for transmitting said registered voice signals from said means for registering voice signals to said means for continuously storing the registered voice signals.

2. A medical workstation as claimed in claim 1 further comprising a device adapted to be worn by a person attending a patient, said device carrying said means for electrically registering voice signals, and wherein said means for electrically registering voice signals is mounted on said device so as to be adapted to be disposed substantially in a mouth region of said person.

3. A medical workstation as claimed in claim 1 wherein said means for transmitting said voice signals comprise an electrical connecting line between said means for electrically registering voice signals and said means for continuously storing the registered voice signals.

4. A medical workstation as claimed in claim 1 wherein said means for transmitting comprise a wireless transmitter connected to said means for electrically registering voice signals and a wireless receiver, which receives signals wirelessly from said wireless transmitter, connected to said means for continuously storing the registered voice signals.

5. A medical workstation as claimed in claim 1 wherein said means for continuously storing the registered voice signals comprise a registration unit having a storage medium on which said voice signals are stored, and means for acoustically playing back the voice signals stored on said storage medium.

* * * * *